(12) United States Patent
Gross et al.

(10) Patent No.: US 8,204,716 B2
(45) Date of Patent: Jun. 19, 2012

(54) SYSTEM AND METHOD FOR CHARACTERIZING VIBRATION OF A RACK STRUCTURE

(75) Inventors: Kenny C. Gross, San Diego, CA (US);
Aleksey M. Urmanov, La Jolla, CA (US); Anton A. Bougaev, La Jolla, CA (US); David K. McElfresh, San Diego, CA (US)

(73) Assignee: Oracle America, Inc., Redwood City, CA (US)

( * ) Notice: Subject to any disclaimer, the term of this patent is extended or adjusted under 35 U.S.C. 154(b) by 380 days.

(21) Appl. No.: 12/491,637

(22) Filed: Jun. 25, 2009

(65) Prior Publication Data

US 2010/0326193 A1 Dec. 30, 2010

(51) Int. Cl.
*G01H 13/00* (2006.01)
(52) U.S. Cl. ....................................... 702/183
(58) Field of Classification Search ................... 702/183
See application file for complete search history.

(56) References Cited

U.S. PATENT DOCUMENTS 7,565,226 B1 7/2009 Cooley et al.
2004/0027799 A1 2/2004 King et al.

OTHER PUBLICATIONS

N. Tandon, Vibration and noise analysis of computer hard disk drives, Elsevier Ltd., Nov. 28, 2005, p. 16-25.*

* cited by examiner

*Primary Examiner* — Tung S Lau
(74) *Attorney, Agent, or Firm* — Brooks Kushman P.C.

(57) ABSTRACT

A system for characterizing vibration of a rack structure having at least one hard disk drive disposed therein and a vibration exciter operatively associated with the rack structure includes one or more computers. The one or more computers are configured to command the vibration exciter to provide vibration input to the rack structure and to command a plurality of reads from the at least one hard disk drive such that, for each of the plurality of reads, data stored on the at least one hard disk drive is retrieved from the at least one hard disk drive. The one or more computers are also configured to obtain read rate information related to the plurality of reads and to identify at least one resonant frequency of the rack structure based on the read rate information.

8 Claims, 8 Drawing Sheets

US 8,204,716 B2

SYSTEM AND METHOD FOR CHARACTERIZING VIBRATION OF A RACK STRUCTURE

BACKGROUND

As known in the art, resonance is the state of a system in which the frequency of the excitation force is close to the system's natural frequency. Small periodic driving forces can produce large amplitude vibrations at these frequencies. Mechanical structures, such as bridges, power plants, computer racks and servers, etc., may be subjected to multi-frequency vibration input and system response measured via accelerometers at various locations to identify resonant frequencies.

SUMMARY

A system for characterizing vibration of a rack structure having at least one hard disk drive disposed therein and a vibration exciter operatively associated with the rack structure includes one or more computers. The one or more computers are configured to command the vibration exciter to provide vibration input to the rack structure and to command a plurality of reads from the at least one hard disk drive such that, for each of the plurality of reads, data stored on the at least one hard disk drive is retrieved from the at least one hard disk drive. The one or more computers are also configured to obtain read rate information related to the plurality of reads and identify at least one resonant frequency of the rack structure based on the read rate information.

A method for characterizing vibration of a rack structure having at least one hard disk drive disposed therein includes commanding a vibration exciter operatively associated with the rack structure to provide vibration input to the rack structure and commanding a plurality of writes to the at least one hard disk drive such that, for each of the plurality of writes, data is written to the at least one hard disk drive. The method also includes obtaining write rate information related to the plurality of writes and identifying at least one resonant frequency of the rack structure based on the write rate information.

A method for characterizing vibration of a rack structure includes commanding a vibration exciter operatively associated with the rack structure at a first location to provide step-wise mono-frequency vibration input to the rack structure. The method also includes obtaining response data to the vibration input from an accelerometer operatively associated with the rack structure at the first location and from another accelerometer operatively associated with the rack structure at a second location. The method further includes identifying at least one resonant frequency of the rack structure based on the response data from the accelerometers.

While example embodiments in accordance with the invention are illustrated and disclosed, such disclosure should not be construed to limit the invention. It is anticipated that various modifications and alternative designs may be made without departing from the scope of the invention.

DETAILED DESCRIPTION

Vibration characterization (or analysis) of computer rack structures may be performed to determine if the rack (or any of its structural elements) amplifies or attenuates vibrations. If, for example, any portions of the rack amplify vibrations that are generated by servers inside the rack or AC systems mounted on top of the rack, then the servers may experience I/O throughput problems.

Rack structures may be analyzed by shipping them to a facility with a large programmable shake table, instrumenting them with accelerometers, and subjecting them to vibrational loads via the shake table. Such facilities, however, are not widely available. Additionally, empty racks may exhibit different vibrational characteristics as compared with full racks, and servers loaded at the test site may be different in type and number than those at the customer site.

Embodiments described herein may seek to quantify vibrational characteristics of computer rack structures without the use of shake tables. These structures may thus be analyzed in place ("in situ") and need not be sent off-site. Rack structures may thus be tested prior to customer delivery to certify they are resonance free. Rack structures may also be tested before and after the addition of racks or servers to assess how these changes impact vibrational behavior. Other scenarios are also possible.

In some embodiments, a rack structure may be instrumented with accelerometers at various locations and subjected to a mono-frequency vibration input (e.g., a sine wave of a particular frequency). The response of the system, as measured by accelerometers remote from the input location, may be compared with the response of the system as measured by an accelerometer at the input location. The mechanical coupling between each of the remote accelerometer locations and the input location may then be determined in a known fashion. In other embodiments, hard disk drives (HDDs) within a rack structure may be instrumented with known telemetry tools that monitor, for example, I/O rate, latency, etc. and subjected to vibration input via the rack structure. Marked decreases in I/O rate, e.g., decreases greater than 15%, at particular frequencies may indicate a resonance condition at those frequencies as discussed, for example, in more detail below with reference to FIG. 12.

Direct Vibration Analysis

Figure 1:
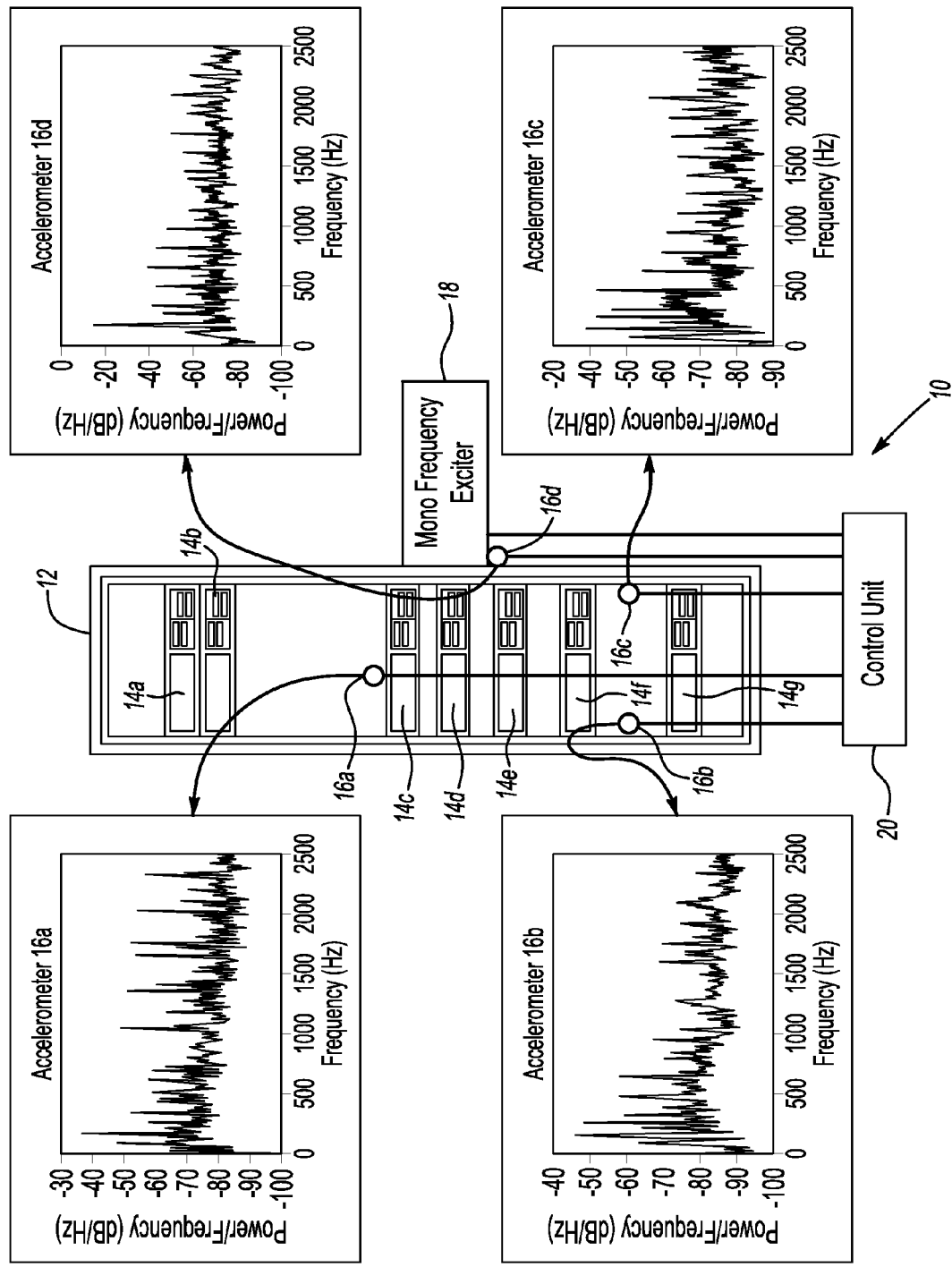
FIG. 1 is a schematic diagram of a rack structure and an embodiment of a vibration characterization system.

Referring now to FIG. 1, a rack structure 10 may include a rack 12 and a plurality of servers 14a through 14g. The rack structure 10 has been instrumented with a plurality of accelerometers 16a through 16d and a mono-frequency vibration exciter 18. In this example, the accelerometer 16a is located on top of the server 14c, the accelerometer 16b is located on the left pole of the rack 12, the accelerometer 16c is located on the right pole of the rack 12, and the accelerometer 16d is located adjacent to the mono-frequency exciter 18. In other examples, the accelerometers 16a through 16d and exciter 18 may be located as desired. Of course, any suitable number of accelerometers may be used.

A control unit 20 (e.g., computer(s), controller, hardware, firmware executing on a processor, software executing on a processor, etc.) controls the operation of the exciter 18 and receives data from the accelerometers 16a through 16d. FIG. 1 includes example plots illustrating the ambient vibration (in the absence of input by the exciter 18) caused by operation of the servers 14a through 14g, etc. and measured by the accelerometers 16a through 16d. The rack structure 10 of FIG. 1 operates in an environment having many superimposed sources of vibration.

The control unit 20, in some embodiments, may command the exciter 18 to provide a step-wise mono-frequency input (of fixed amplitude) over a specified frequency range. For example, the control unit 20 may command the exciter 18 to provide input at frequencies from 100 Hz to 500 Hz in 1 Hz increments (e.g., 100 Hz, 101 Hz, 102 Hz, . . . , 498 Hz, 499 Hz, 500 Hz) during a period of 30 seconds. Other ranges, increments and durations are also possible. Data from the accelerometers 16a, 16b, 16c may then be compared with data from the accelerometer 16d, in a known fashion described with reference to FIGS. 2 through 6 below, to determine the mechanical coupling or tendency for vibration to propagate from the location of the exciter 18 to the locations instrumented with the accelerometers 16a, 16b, 16c.

Figure 2:
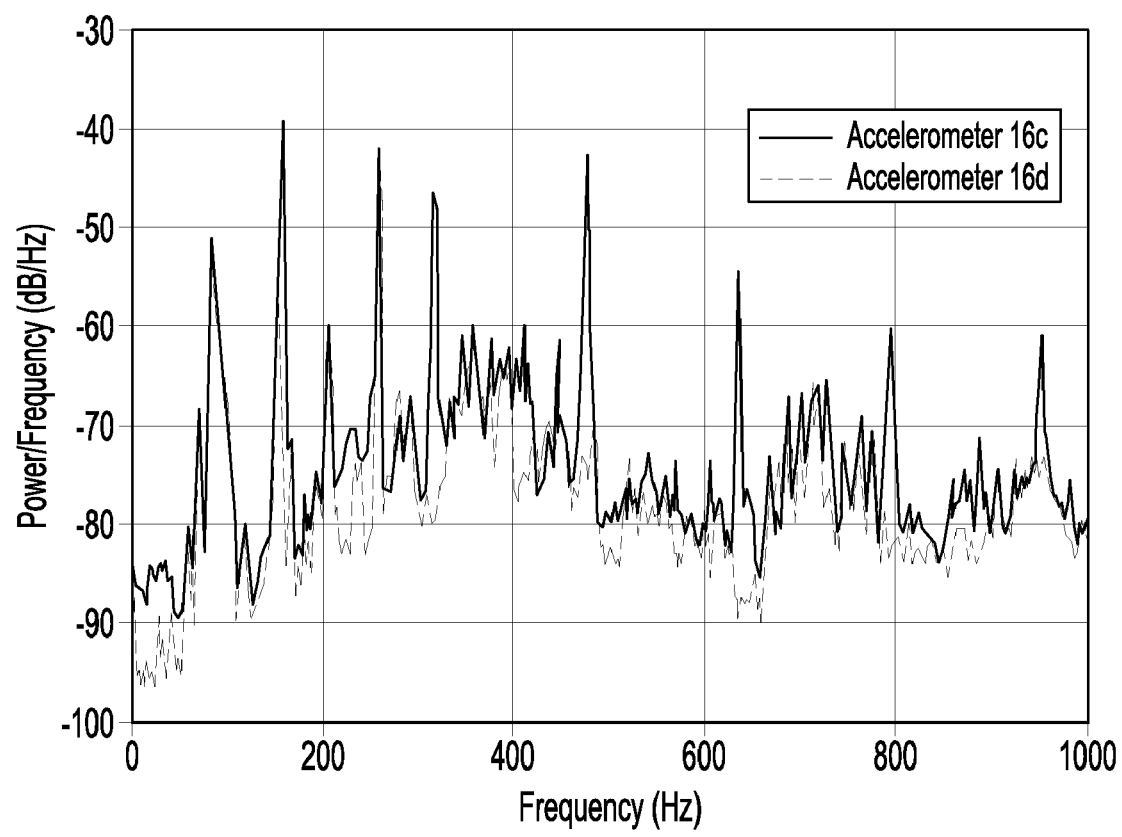
FIGS. 2 through 4 are example plots of the fast Fourier transform of accelerometer data collected from the rack structure of FIG. 1.

Referring now to FIG. 2, the fast Fourier transform of data measured by the accelerometer 16c has been overlaid onto data measured by the accelerometer 16d. Note that the full spectrum data measured by the accelerometer 16d, in this example, was gathered 1 Hz at a time over a 30 second period. The temporally spaced mono-frequency inputs have resulted in prominent peaks at several frequencies, e.g., approximately 160 Hz, approximately 475 Hz.

Figure 3:
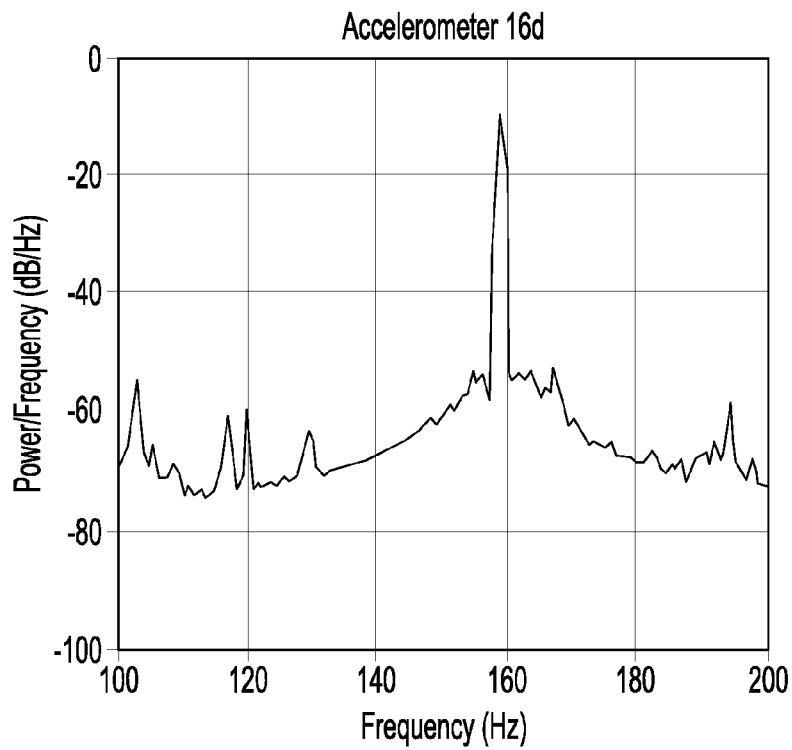
Figure 4:
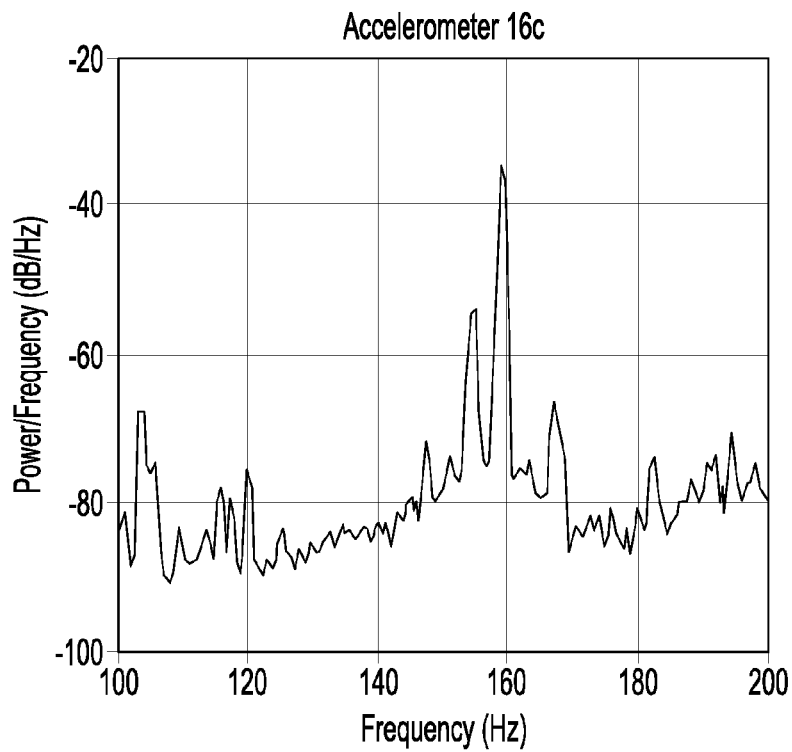

Referring now to FIGS. 3 and 4, the control unit 20 illustrated in FIG. 1 has determined, in a known fashion, the power spectral density (which describes how the power of a signal or time series is distributed with frequency) of the data measured by the accelerometers 16d, 16c respectively.

Figure 5:
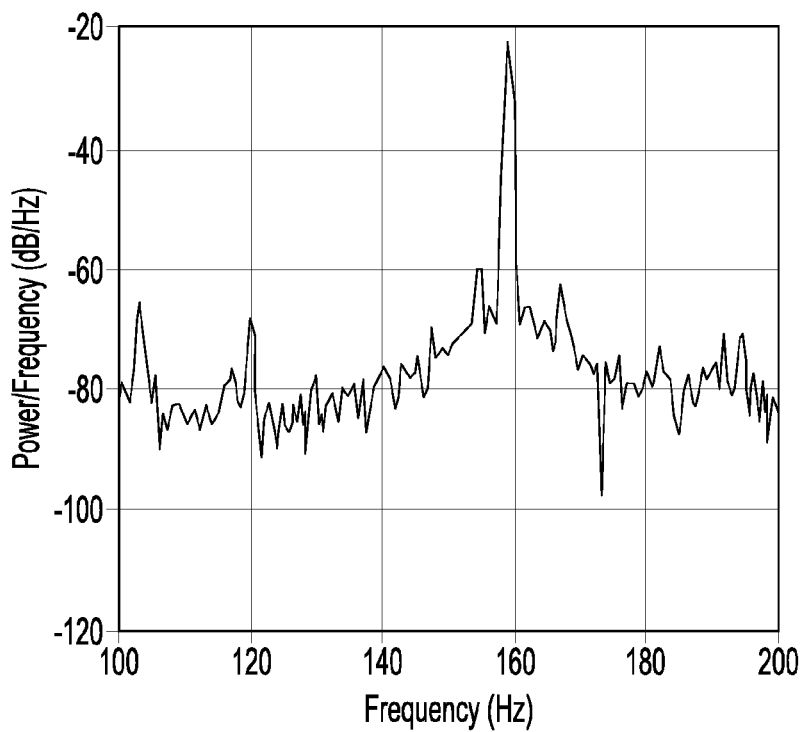
FIG. 5 is an example plot of the cross power spectral density associated with the data of FIGS. 3 and 4.

Referring now to FIG. 5, the control unit 20 has determined, in a known fashion, the cross power spectral density of the power spectral density data of FIGS. 3 and 4.

Figure 6:
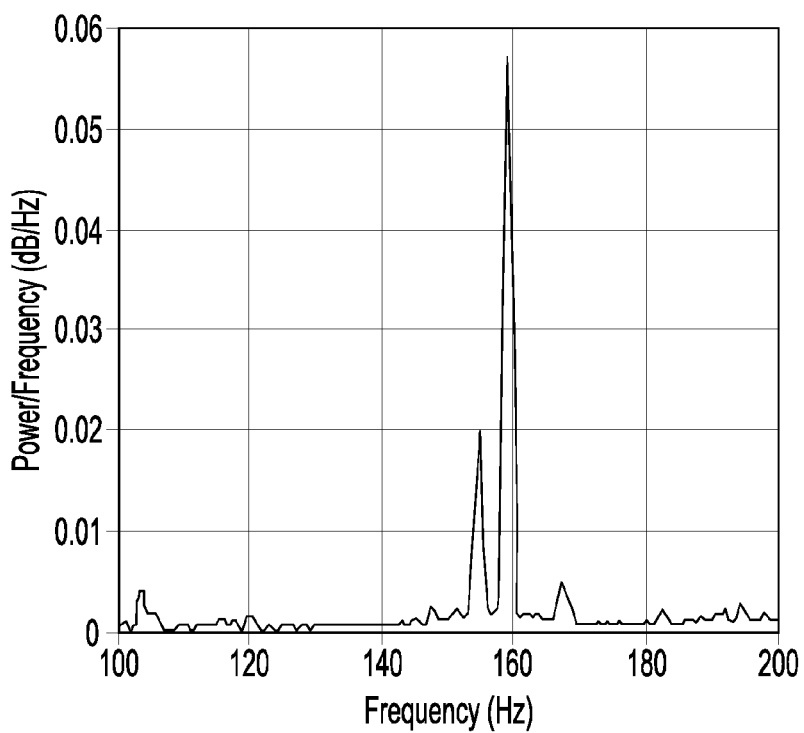
FIG. 6 is an example plot of the coupling coefficient associated with the cross power spectral density data of FIG. 5.

Referring now to FIG. 6, the control unit 20 has determined, in a known fashion, the coupling coefficient of the cross power spectral density data of FIG. 5. A prominent peak, e.g., a peak exceeding 0.03 in this embodiment, (other threshold values, however, may also be used) occurs at around 160 Hz. This suggests that the input location of the exciter 18 illustrated in FIG. 1 and the right pole of the mechanical rack 12 are strongly mechanically coupled at frequencies around 160 Hz. To avoid issues associated with the operation of the servers 14n, vibration inputs having a frequency of about 160 Hz should be avoided. Similar analysis with respect to the data measured by the accelerometers 16a, 16b may also performed.

Indirect Vibration Analysis

Figure 7:
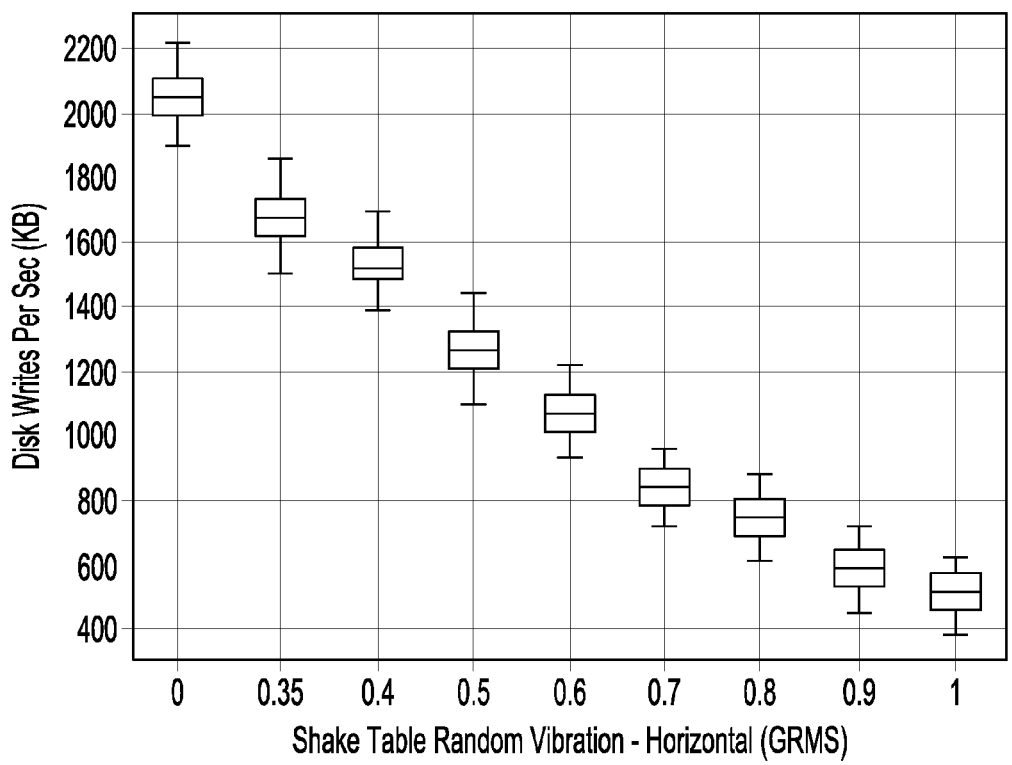
FIG. 7 is an example plot of hard disk drive (HDD) throughput versus shake table vibration.

Referring to FIG. 7, HDD write throughput is plotted as a function of vibration level. The data for this plot was generated by measuring HDD write speed (in KB/sec) for various GRMS inputs after securing the HDD to a shake table (such that the wide area of the HDD was parallel to the shake table surface). As known in the art, shake tables provide random vibrations. HDD throughput appears to decrease as random vibration increases.

Figure 8:
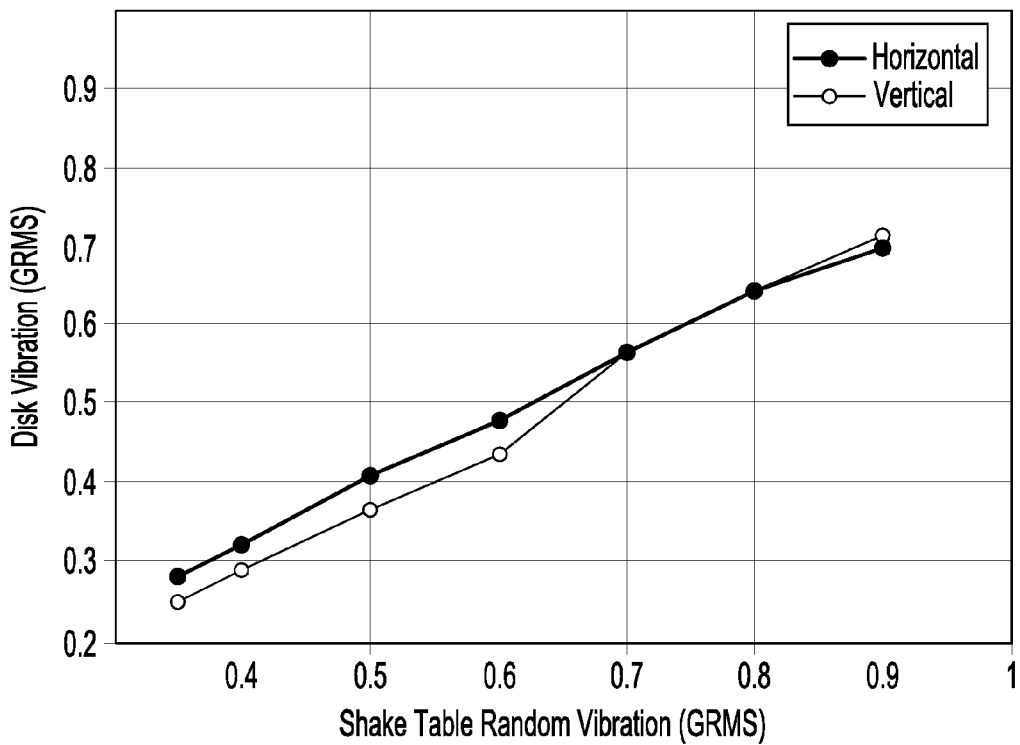
FIG. 8 is an example plot of HDD vibration versus shake table vibration.

Referring now to FIG. 8, HDD vibration was correlated with shake table vibration (vertical and horizontal). HDD vibration appears to exhibit a high degree of correlation with shake table vibration.

The decrease in HDD throughput as a function of shake table vibration illustrated in FIG. 7 appears to result from vibration of the HDD. Current read/write magnetic heads are expected to read/write tracks of a HDD having widths less than about 20 nanometers while floating about 7 nanometers above the disk surface. The random vibration of the HDD may cause the magnetic head to skip tracks. Vibration, therefore, may affect the performance of read/write heads.

As known in the art, a cache may be a temporary storage area where frequently accessed data can be stored for rapid access. Once the data is stored in the cache, it can be subsequently used by accessing the cached copy rather than re-fetching or re-computing the original data. Currently, there may be caches in the OS domain, caches in the network, caches inside the disk drives, etc. Caches are usually based on solid state flash technology, which has little to no sensitivity to vibration. Consequently, it is possible to get different inferred vibration metrics depending on, for example, whether a particular OS enables or disables a domain cache by default. Similarly, a vibration assessment script run on a system via remote login may yield completely different results compared with the same script run via a local console simply because of the presence/absence of a network cache.

Figure 9:
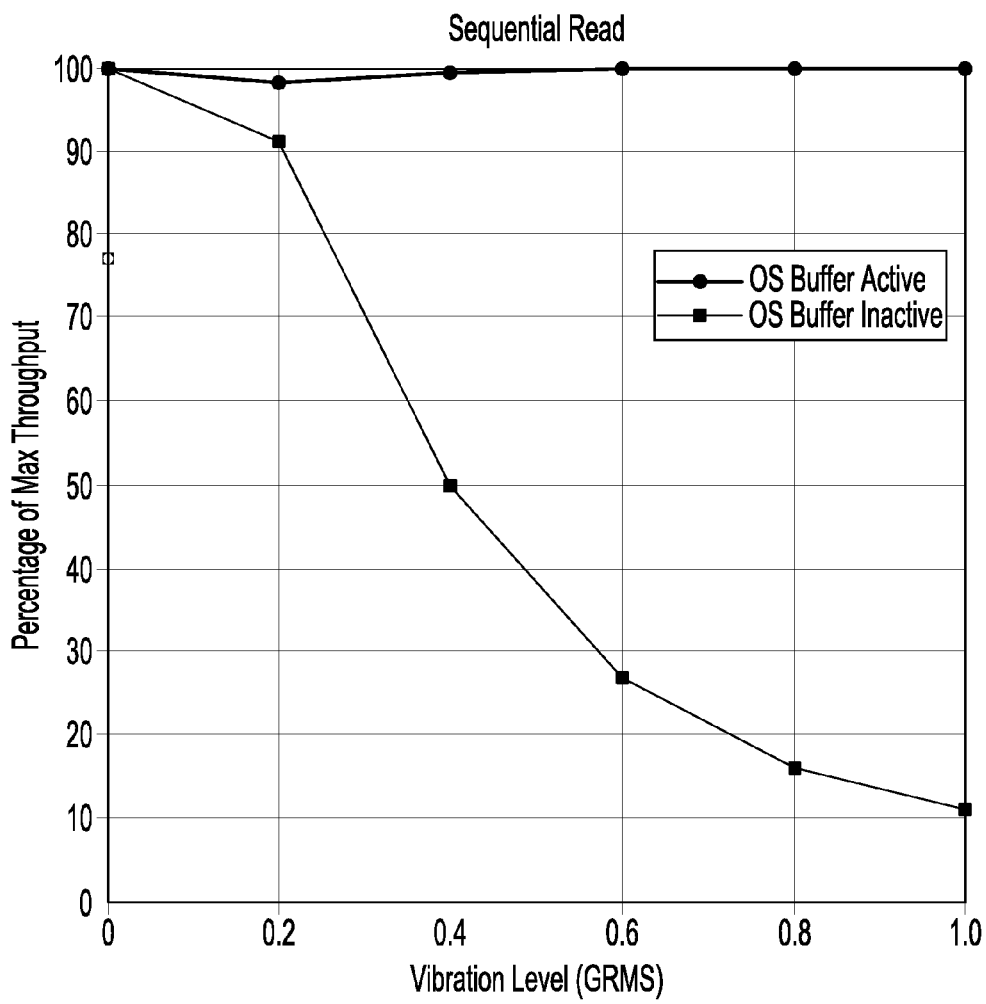
FIG. 9 is an example plot of percentage of HDD maximum throughput versus vibration level.

Referring now to FIG. 9, the percentage of maximum throughput for an HDD subjected to differing levels of vibration (via a shake table) remained relatively unchanged for read/write activity with an active OS buffer. The percentage of maximum throughput for the same HDD subjected to differing levels of vibration (via the shake table), however, decreased for read/write activity with an inactive OS buffer. Buffers (caches, etc.) may mask the effects of vibration on I/O rate and thus confound attempts to infer disk vibration levels based on I/O rate.

In certain embodiments, a vibration-calibrated disk read/write activity generator that bypasses caches in the OS, network and/or HDD may be used in conjunction with system telemetry gathered while the system is subjected to vibration to determine mechanical coupling or tendency for vibration to propagate. Time and effort need not be spent on instrumenting the system with accelerometers. Additionally, more consistent and reproducible results may be obtained regardless of the presence/absence of caches, for example, flash-based caches, in the system.

In one example, random reads are performed at the outer tracks of a disk drive while the rack structure housing the disk drive is subjected to vibration input. (The vibration input may be of a level that, unless amplified, does not substantially impact read rates.) Varying block sizes, e.g., block sizes increasing from 4 KB to 256 KB or greater, may be used to ensure that pre-fetching data from any read caches is not beneficial to performance by causing cache misses to occur. Hence for each of the reads, data is retrieved from the drive rather than the cache. Substantial decreases in read rate, e.g., decreases in read rate greater than 20%, may be observed at resonant frequencies within the rack structure.

In another example, random (as opposed to sequential) writes are performed at the outer tracks of a disk drive using random data patterns while the rack structure housing the disk drive is subjected to vibration input. Writes may be more sensitive to vibration than reads. (Data from a file or a constant write pattern is not written.) The random writes ensure that caches are not involved in this process. Substantial decreases in write rate may be observed at resonant frequencies within the rack structure.

In yet another example, both reads and writes are performed on the disk raw device rather than the block (or logical) device to ensure that any OS buffers are not involved in this process while the rack structure housing the disk drive is subjected to vibration input. Resulting read and/or write rates may be used to identify resonant frequencies within the rack structure.

Figure 10:
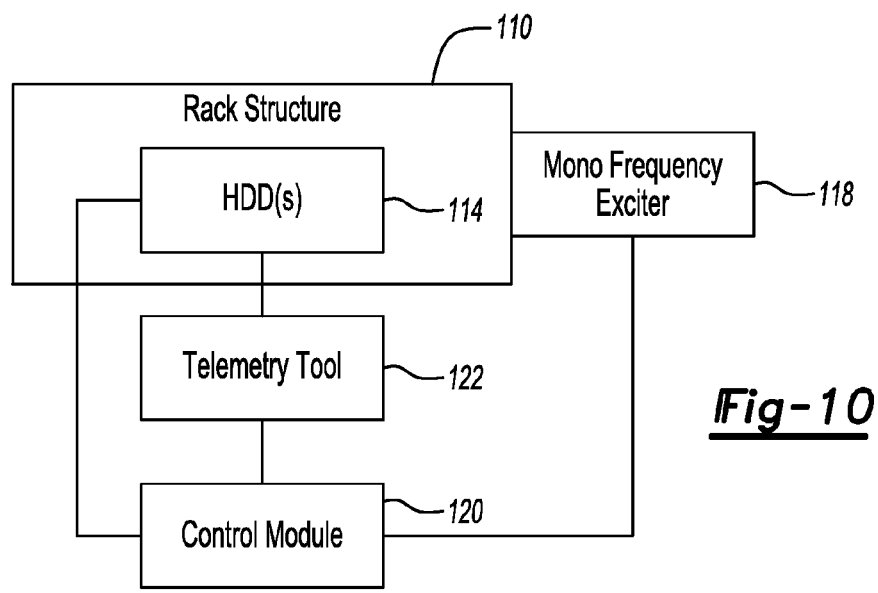
FIG. 10 is a schematic diagram of another rack structure and another embodiment of a vibration characterization system.

Referring now to FIG. 10, numbered elements of FIG. 10 that differ by 100 relative to the numbered elements of FIG. 1 may have similar descriptions to the numbered elements of FIG. 1. A rack structure 110 may include one or more HDDs 114. A mono-frequency vibration exciter 118 may be operatively mounted to the rack structure 110. A control module 120, as explained below, may command the exciter 118 to subject the rack structure 110 to, for example, a step-wise mono-frequency vibration input. (As mentioned above, the vibration input may be of a level that does not substantially impact I/O rate unless amplified.) A telemetry tool 122 may measure various performance parameters, such as I/O rate, latency, etc., associated with the one or more HDDs 114 and report this information to the control module 120. The control module 120, as explained below, may use the telemetry information to identify resonant frequencies of the rack structure 110 based on the I/O rate of the one or more HDDs 114.

Figure 11:
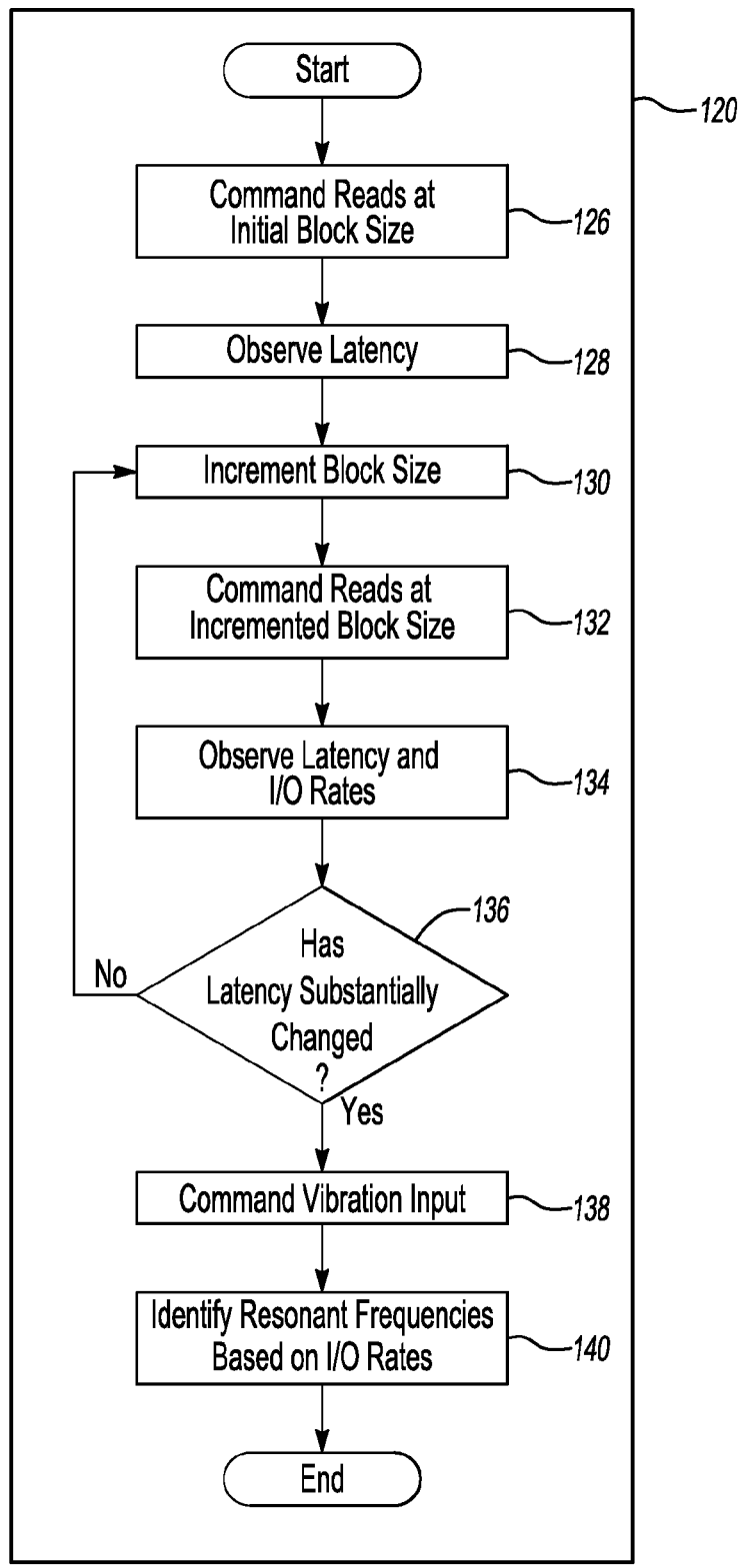
FIG. 11 is a flow chart illustrating an example algorithm for determining resonant frequencies of the rack structure of FIG. 10.

Referring now to FIGS. 10 and 11, the control module 120 commands reads via, for example, a load generation script (e.g., a script that generates a specified number of reads per second) of the one or more HDDs 114 at an initial block size, e.g., 12 KB, at operation 126. This initial block size may be specified by a user or preset within the control module 120. In some embodiments, the reads may be commanded from a specified set of tracks on the one or more HDDs 114. This may reduce noise in the data associated with movement of the read head.

At operation 128, the control module 120 observes the latency associated with the reads based on information received from the telemetry tool 122.

At operation 130, the control module 120 increments the block size by, for example, 4 KB.

At operation 132, the control module 120 commands reads of the one or more HDDs 114 at the incremented block size, e.g., 16 KB.

At operation 134, the control module 120 observes the latency and I/O rate associated with the reads based on information received from the telemetry tool 122.

At operation 136, the control module 120 determines whether the latency associated with the reads commanded at operation 132 has substantially changed, e.g., doubled, etc., relative to the reads commanded at operation 126. If no, the control module 120 returns to operation 130 and increments the block size by, for example, another 4 KB, etc. (In certain embodiments, a maximum block size may be specified such that if a substantial change in latency is not observed by the time the maximum block size is achieved, the process continues to operation 138. This maximum block size may be reached, for example, in circumstances where there are no active caches and/or minimal ambient vibration.)

If operation 136 determines that latency has substantially changed, the control module 120 commands the exciter 118 to provide a vibration input to the rack structure 110 at operation 138. For example, the control unit 120 may command the exciter 118 to provide a step-wise (fixed amplitude) monofrequency input from 50 Hz to 750 Hz in 2 Hz increments (e.g., 50 Hz, 52 Hz, 54 Hz, . . . , 746 Hz, 748 Hz, 750 Hz) during a 50 second period. Other ranges, increments and durations are also possible.

Figure 12:
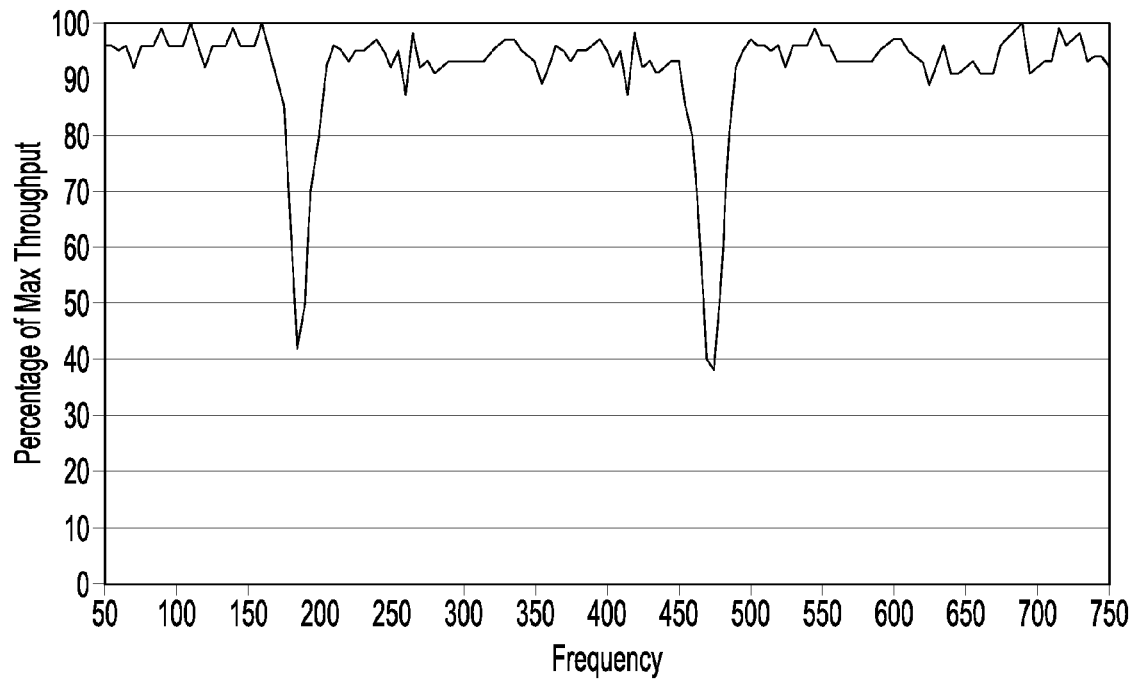
FIG. 12 is an example plot of percentage of HDD maximum throughput versus frequency.

At operation 140, the control module 120 identifies resonant frequencies or mechanical coupling based on read rate information gathered by the telemetry tool 122 during the 50 second period. FIG. 12, for example, plots percentage of max throughput versus frequency. Prominent valleys occur at about 185 Hz and 475 Hz. As discussed with reference to FIG. 9, throughput decreases as vibration level increases. Because the exciter 118 provides vibration input of a fixed amplitude that, unless amplified, does not substantially impact read rate, the rack structure 110 appears to amplify this input (at least in the vicinity of the one or more HDDs 114) at frequencies around 185 Hz and 475 Hz. To avoid issues associated with the operation of the one or more HDDs 114, vibration inputs having a frequency of about 185 Hz or 475 Hz should be avoided.

The iterative process of incrementing read block size and observing corresponding latencies described above may be used to determine when caches within a system are being bypassed. If, for example, the latencies associated with read commands of block sizes between 4 KB and 128 KB remain relatively unchanged, one can assume that caches are in use. If the latencies associated with read commands of block sizes greater than 128 KB substantially change (relative to those of block sizes between 4 KB and 128 KB), one can assume that caches are no longer in use, and that data is being read directly from disk. Of course, if a particular block size is known (through testing or experience) to be of sufficient size such that caches are bypassed during reads, that block size, in certain embodiments, may be specified at the beginning of the process. In such embodiments, the iterative process of incrementing read block size and observing corresponding latencies may be omitted. Other scenarios are also possible.

Figure 13:
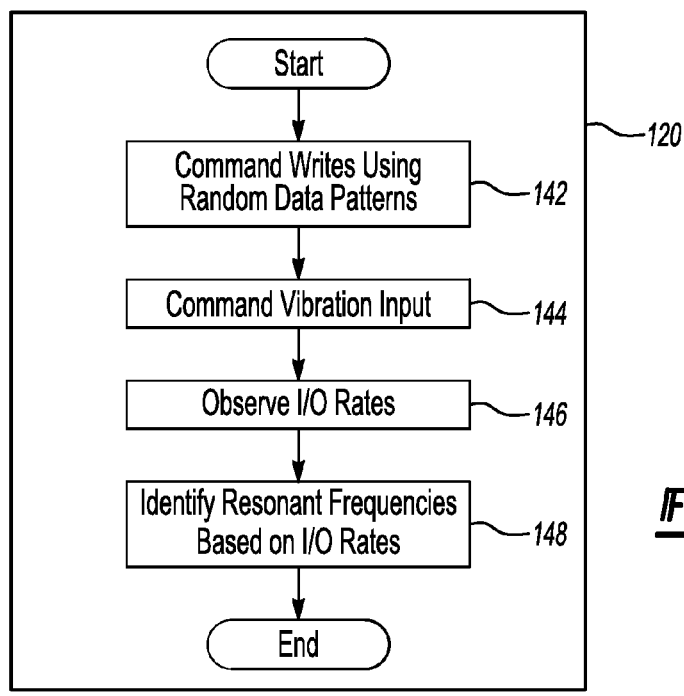
FIG. 13 is a flow chart illustrating another example algorithm for determining resonant frequencies of the rack structure of FIG. 10.

Referring now to FIGS. 10 and 13, the control module 120 commands random data writes to the one or more HDDs 114 at operation 142. In some embodiments, the writes may be commanded to a specified set of tracks on the one or more HDDs 114. As explained above, this may reduce noise in the data associated with movement of the write head. The data for the writes are generated, for example, via a random number generator or pseudo random number generator. As apparent to those of ordinary skill, the pseudo random number generator may be used in circumstances where repeatability in testing is desired. The same seed may used to generate the same sequence of pseudo random numbers between tests.

At operation 144, the control module 120 commands the exciter 118 to provide, for example, step-wise mono-frequency vibration input to the rack structure 110.

At operation 146, the control module 120 observes the I/O rate associated with the writes based on information received from the telemetry tool 122.

At operation 148, the control module 120 identifies resonant frequencies or mechanical coupling based on the I/O rate provided by the telemetry tool 122 as discussed above.

As apparent to those of ordinary skill, the algorithms disclosed herein may be deliverable to a processing device in many forms including, but not limited to, (i) information permanently stored on non-writable storage media such as ROM devices and (ii) information alterably stored on writeable storage media such as floppy disks, magnetic tapes, CDs, RAM devices, and other magnetic and optical media. The algorithms may also be implemented in a software executable object. Alternatively, the algorithms may be embodied in whole or in part using suitable hardware components, such as Application Specific Integrated Circuits (ASICs), state machines, controllers or other hardware components or devices, or a combination of hardware, software and firmware components.

While embodiments of the invention have been illustrated and described, it is not intended that these embodiments illustrate and describe all possible forms of the invention. The words used in the specification are words of description rather than limitation, and it is understood that various changes may be made without departing from the spirit and scope of the invention.

What is claimed is:

1. A system for characterizing vibration of a rack structure having (i) a rack with at least one hard disk drive disposed thereon and (ii) a vibration exciter operatively associated with the rack structure, the system comprising:
one or more computers configured to (i) command the vibration exciter to provide step-wise mono-frequency vibration input of fixed amplitude to the rack structure, (ii) command a plurality of reads from the at least one hard disk drive such that, for each of the plurality of reads, data stored on the at least one hard disk drive is retrieved from the at least one hard disk drive, (iii) obtain read rate information related to the plurality of reads, and (iv) identify at least one resonant frequency of the rack structure based on the read rate information.

2. The system of claim 1 wherein identifying at least one resonant frequency of the rack structure based on the read rate information includes identifying a decrease in read rate relative to a maximum read rate at a particular frequency.

3. The system of claim 1 wherein the one or more computers are further configured to command a plurality of sequential reads of increasing block size from the at least one hard disk drive and obtain latency information related to the plurality of sequential reads of increasing block size.

4. The system of claim 1 wherein the plurality of reads are commanded from a specified set of tracks on the at least one hard disk drive.

5. The system of claim 1 wherein the vibration input is of a level that does not generally impact read rate in the absence of rack structure resonance.

6. The system of claim 2 wherein the decrease in read rate is greater than 15%.

7. The system of claim 3 wherein the one or more computers are further configured to determine whether a particular block size is of a sufficient size such that data stored on the at least one hard disk drive is retrieved from the at least one hard disk drive based on the latency information.

8. The system of claim 4 wherein the specified set of tracks are outermost tracks of the at least one hard disk drive.

* * * * *